US011517244B1

(12) United States Patent
Sadanand et al.

(10) Patent No.: US 11,517,244 B1
(45) Date of Patent: Dec. 6, 2022

(54) SIGNAL PROCESSING TO COMPUTE 3D SPATIAL EEG MAP FROM 2D EEG DATA

(71) Applicants: Venkatraman Sadanand, Loma Linda, CA (US); Siddharth Sadanand, Toronto (CA)

(72) Inventors: Venkatraman Sadanand, Loma Linda, CA (US); Siddharth Sadanand, Toronto (CA)

(*) Notice: Subject to any disclaimer, the term of this patent is extended or adjusted under 35 U.S.C. 154(b) by 1059 days.

(21) Appl. No.: 14/830,567

(22) Filed: Aug. 19, 2015

Related U.S. Application Data

(60) Provisional application No. 62/041,986, filed on Aug. 26, 2014.

(51) Int. Cl.
*A61B 5/374* (2021.01)
*A61B 5/369* (2021.01)
*A61B 5/00* (2006.01)

(52) U.S. Cl.
CPC ............ *A61B 5/369* (2021.01); *A61B 5/6814* (2013.01); *A61B 5/7239* (2013.01); *A61B 5/7257* (2013.01)

(58) Field of Classification Search
None
See application file for complete search history.

(56) References Cited

U.S. PATENT DOCUMENTS

| | | | | |
|---|---|---|---|---|
| 8,326,418 B2* | 12/2012 | Sommer | ................ | A61N 1/056 607/15 |
| 2005/0007091 A1* | 1/2005 | Makeig | ................ | A61B 5/048 324/76.13 |
| 2009/0143045 A1* | 6/2009 | Graves | ................ | A61B 5/02055 455/404.1 |
| 2010/0185108 A1* | 7/2010 | Vullings | ............ | A61B 5/04011 600/511 |
| 2011/0004115 A1* | 1/2011 | Shahaf | ................ | A61B 5/04009 600/544 |
| 2012/0271151 A1* | 10/2012 | LaVoilette | ................ | A61B 5/06 600/411 |
| 2013/0109996 A1* | 5/2013 | Turnbull | .............. | A61B 5/7264 600/544 |

(Continued)

OTHER PUBLICATIONS

What is trilateration?, Jan. 2, 2010, Mio, pp. 1.*

(Continued)

*Primary Examiner* — Etsub D Berhanu
(74) *Attorney, Agent, or Firm* — Womble Bond Dickinson (US) LLP

(57) ABSTRACT

A method of deriving depth EEG data from non-invasive 2D EEG data is described. The method receives several EEG scalp signals, each of which is produced by a contact of an EEG recording device. The method converts each EEG scalp signal into multiple frequency band signals. The method identifies a set of contacts that have similar signal fragments in frequency band signals for a particular frequency band. The method determines relative time delay in frequency band signal arrival at the set of contacts. The method determines relative radius of sphere for the set of contacts based on the relative time delay in frequency band signal arrival at the set of contacts. The method then determines a signal source location by performing trilateration on the set of contacts using locations of the set of contacts and the relative radius of sphere for the set of contacts.

18 Claims, 8 Drawing Sheets

(56) References Cited

U.S. PATENT DOCUMENTS

| | | | | |
|---|---|---|---|---|
| 2013/0304407 A1* | 11/2013 | George | ......... | G01R 25/00 |
| | | | | 702/72 |
| 2014/0088395 A1* | 3/2014 | Dubois | ......... | A61B 5/046 |
| | | | | 600/382 |
| 2014/0135642 A1* | 5/2014 | Ekpar | ......... | A61B 5/7264 |
| | | | | 600/544 |
| 2015/0035670 A1* | 2/2015 | Cyr | ......... | G08B 29/185 |
| | | | | 340/506 |
| 2015/0297106 A1* | 10/2015 | Pasley | ......... | A61B 5/048 |
| | | | | 600/378 |
| 2016/0231426 A1* | 8/2016 | Smith | ......... | G01S 17/86 |

OTHER PUBLICATIONS

Willy Hereman, Determination of a Position in Three Dimensions Using Trilateration and Approximate Distances, Oct. 1995, Colorado School of Mines, MCS-95-07, pp. 1-21.*

Carmen Vidaurre, Time Domain Parameters as a feature for EEG-Based Brain Computer Interfaces, 2009, Neural Networks, pp. 1313-1319.*

M.G. Wentrup, EEG Source Localization for Brain-Computer Interfaces, Apr. 18, 2005, Neural Engineering, pp. v-viii.*

FFT for Spectral Analysis, 2013, MathWorks, pp. 1-2.*

Ralph Bucher, A Synthesizable VHDL Model of the Exact Solution for Three-dimensional Hyperbolic Positioning System, 2002, VLSI Design, vol. 15(2), pp. 507-520 (Year: 2002).*

\* cited by examiner

SIGNAL PROCESSING TO COMPUTE 3D SPATIAL EEG MAP FROM 2D EEG DATA

CROSS-REFERENCE TO RELATED APPLICATION

This application claims the benefit of the earlier filing date of provisional application No. 62/041,986, filed Aug. 26, 2014.

FIELD

The present invention relates to electroencephalography (EEG) signal processing and in particular to generating a three-dimensional (3D) spatial EEG map from two-dimensional (2D) EEG data.

BACKGROUND

A brain-computer interface (BCI) is a direct communication pathway between the brain and an external device for human-machine interaction. BCIs are often directed at assisting, augmenting, or repairing human cognitive or sensory-motor functions. Brain-computer interfaces can be based on either non-invasive or invasive technologies.

Non-invasive BCI systems rely on electroencephalography (EEG) waveforms recorded over the scalp. The electrical signals emitted by a multitude of neurons, their dendrites, synapses and axons project to the surface. The summation of all these signals appears as the scalp EEG.

Gross movements are initiated deep in the brain. Fine motor control is also achieved deep in the brain. Furthermore, Start and Stop commands arise outside the motor cortex. In addition, color perception and sound sensing are also subcortical functions. Therefore, it is important to tap the information content of subcortical nuclei, synapses and tracts, as they are responsible for refinement, initiation and end of motor movements and perception of specialized senses. Non-invasive scalp EEG-based human-machine interfaces therefore have somewhat limited functional capabilities.

Invasive BCI are based on electrocorticography (ECoG) from the surgical implantation of EEG grids, strips or depth electrodes. The risks of surgery range from stroke, intracranial hemorrhages, paralysis, speech deficits, visual deficits, memory deficits, infection, meningitis, induced seizures, dysphagia and even death. For these reasons, invasive BCI research has been limited to animal studies.

SUMMARY

An apparatus and method to computationally localize deep brain EEG signals using scalp recordings is described. The method computes 3D spatial EEG data using 2D scalp EEG data. Based on this computed spatial EEG data, the method builds a model and prototype for human-machine interactions that can sense actual, imagined or intended movements, sounds and colors. The method records scalp EEGs, and yet derives the spatial resolution of invasive EEGs. The information gained from identifying, characterizing and locating deep brain EEGs can provide fine control for motor movements as well as EEG correlates for vision, speech and sound.

A method of deriving depth EEG data from non-invasive 2D EEG data is described. In an exemplary embodiment, the method receives several EEG scalp signals, each of which is produced by a contact of an EEG recording device. The method converts each EEG scalp signal into multiple frequency band signals. The method identifies a set of contacts that have similar signal fragments in frequency band signals for a particular frequency band. The method determines relative time delay in frequency band signal arrival at the set of contacts. The method determines relative radius of sphere for the set of contacts based on the relative time delay in frequency band signal arrival at the set of contacts. The method then determines a signal source location by performing trilateration on the set of contacts using locations of the set of contacts and the relative radius of sphere for the set of contacts.

In particular, a method of deriving depth electroencephalography (EEG) data from non-invasive 2D EEG data, including receiving a plurality of EEG scalp signals, each of the plurality of EEG scalp signals produced by a contact of an EEG recording device. The method further includes converting each of the plurality of EEG scalp signals into a plurality of frequency band signals, identifying a set of contacts that have similar signal fragments in frequency band signals for a particular frequency band and determining a signal source location by performing trilateration with the set of contacts. The method further includes converting each of the plurality of EEG scalp signals into the plurality of frequency band signals using a filter bank or through a set of Fourier transforms. The method further includes converting the plurality of EEG scalp signals from analog signals into digital signals. The method wherein identifying of the set of contacts that have similar signal fragments includes taking a first derivative of each frequency band signal, and identifying the set of contacts that have similar first derivatives in the frequency band signals for the particular frequency band. The method may further include determining a relative time delay in frequency band signal arrival at the set of contacts. The method may include determining relative radius of sphere for the set of contacts based on the relative time delay in frequency band signal arrival at the set of contacts. In addition, the determining of signal source location by performing trilateration may include performing trilateration on the set of contacts using locations of the set of contacts and the relative radius of sphere for the set of contacts. In some cases, the depth EEG data is created based on the signal source location and the plurality of EEG scalp signals. In addition, the method may include deriving a relationship between a human function and depth EEG data. The method may further include utilizing detected EEG scalp signal changes in a human to drive a machine based on the relationship between human function and depth EEG data. The method may further include grouping multiple proximate contacts into multiple groups of contacts; and for each group of proximate contacts, analyzing the time delays between signals of each contact in the group to determine the direction of the signal source location relative to the group of contacts, wherein the direction of the signal source location is used during performance of trilateration with the group of contacts to determine the signal source location.

In some embodiments, a non-transitory article of manufacture storing instructions for deriving depth to EEG data from non-invasive 2D EEG data is included, wherein the instructions, when performed by a processing device, cause the processing device to process a plurality of EEG scalp signals, each of the plurality of EEG scalp signals produced by a contact of an EEG recording device, convert each of the plurality of EEG scalp signals into a plurality of frequency band signals, identify a set of contacts that have similar signal fragments in frequency band signals for a particular frequency band, and determine a signal source location by performing trilateration with the set of contacts. The non-transitory article of manufacture may further include converting each of the plurality of EEG scalp signals into the plurality of frequency band signals using a filter bank. In some cases, each of the plurality of EEG scalp signals is converted into the plurality of frequency band signals through a set of Fourier transforms. The non-transitory article of manufacture may store further instructions that, when performed by the processing device, cause the processing device to convert the plurality of EEG scalp signals from analog signals into digital signals. The instructions for identifying the set of contacts that have similar signal fragments may cause the processing device to take a first derivative of each frequency band signal identify the set of contacts that have similar first derivatives in the frequency band signals for the particular frequency band. The non-transitory article of manufacture for storing further instructions that, when performed by the processing device, cause the processing device to determine a relative time delay in frequency band signal arrival at the set of contacts. The non-transitory article of manufacture may store further instructions that, when performed by the processing device, cause the processing device to determine relative radius of sphere for the set of contacts based on the relative time delay in frequency band signal arrival at the set of contacts.

In still further embodiments, a system for deriving depth to EEG data from non-invasive 2D EEG data is disclosed. The system may include a set of contacts for placement on a scalp of a patient; and an EEG signal processor, including a set of hardware logic circuits to: receive a plurality of EEG scalp signals, each of the plurality of EEG scalp signals being produced by a contact of an EEG recording device; convert each of the plurality of EEG scalp signals into a plurality of frequency band signals; identify a set of contacts that have similar signal fragments in frequency band signals for a particular frequency band; and determine a signal source location by performing trilateration with the set of contacts.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

Figure 1:
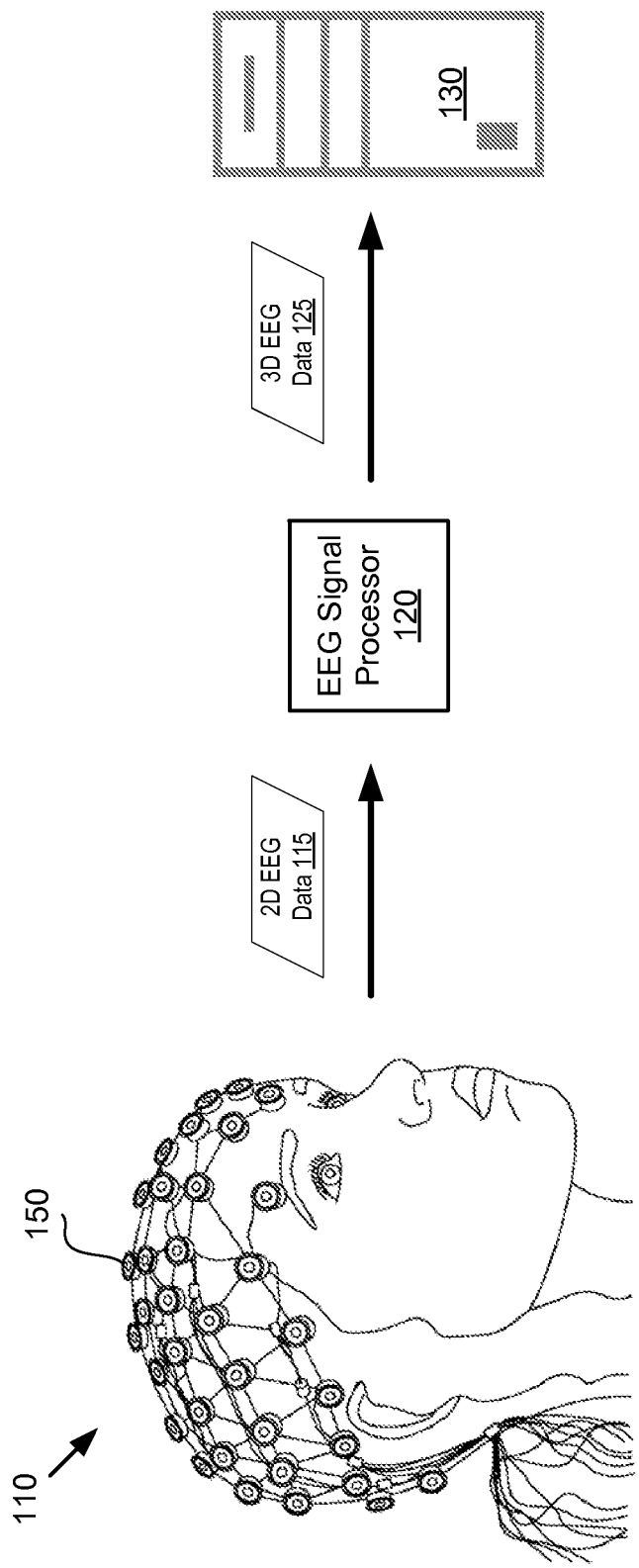
FIG. 1 illustrates an example of using scalp EEG information to drive a non-invasive BCI.

The following Detailed Description of embodiments of the invention makes reference to the accompanying drawings in which like references indicate similar elements, showing by way of illustration specific embodiments of practicing the invention. Description of these embodiments is in sufficient detail to enable those skilled in the art to practice the invention. One skilled in the art understands that other embodiments may be utilized and that logical, mechanical, electrical, functional and other changes may be made without departing from the scope of the present invention. The following Detailed Description is, therefore, not to be taken in a limiting sense, and the scope of the present invention is defined only by the appended claims.

The present disclosure is based on the following six properties and observations about the brain and EEG. First, scalp EEG is the result of electrical activity in the brain. This activity is predominantly from axonal and synaptic discharges rather than neuronal. Therefore, EEG changes with movements or thoughts or sensory inputs are mostly the result of synaptic discharges and axonal transmission of action potentials. An EEG is the sum of several electrical potentials generated in the extracellular space. The most important source of extracellular current flow is synaptic activity. Non-synaptic activity does not contribute significantly to scalp EEG. Eventually, these deep electrical signals come to the surface and the synchronous firing of an estimated at least 108 signals are required to record a visible EEG in the scalp over an area of 6 cm².

Second, action potentials are best approximated as a Triangle wave function. An example of the triangle wave function is $$\delta(t) = \begin{cases} 1 - |t|, & |t| \le 1 \\ 0, & \text{otherwise} \end{cases}$$

whose Fourier Transform $\mathfrak{F}(f)$ is the function $$\left(\frac{\sin(\pi f)}{\pi f}\right)^2$$

Therefore, these electrical signals emanating from the synapses, axons and neurons are primarily sinusoidal waves in the frequency domain that are summed to generate the EEG.

Third, since the scalp EEG is a sum of several deep action potential generators, it has often been thought that it is not easy to determine the location of the deep EEG generators based on the scalp EEG. This is called the inverse problem. An approach to the inverse problem is proposed in this disclosure using the principle of Trilateration. This approach is based on the realistic assumption that the electrical signal generators deep in the brain synapses have unique frequency signatures based on function and location.

Fourth, the brain's electrical impedance is a function of the frequency of the traversing signal. The property is similar to a capacitor—higher frequencies have lower impedance. Electrical signals propagating in exactly opposite directions can cancel each other, resulting in, for example, two signals not being detected at the surface by a single electrode (contact) of the EEG recording device. However, another electrode (contact) at a different location may detect the same two signals since the propagation vector of one or both of the signals from the second electrode may have changed such that the signals no longer cancel each other.

Fifth, in addition to the properties above, brain impedance decreases by about 5% in areas of the brain that are involved in functional activity due to the increased flow of blood in that area, and increases by about 10% in areas of the brain that are experiencing seizures due to cell swelling. The fourth and fifth properties together mean that regions of the brain that are functionally active emit electrical signals whose higher frequency components face lower impedance and hence are more prominent on the surface.

Sixth, electrical activity in the depths as well as the cortex is associated with fine control of movements and responses to sensory inputs. For example, gross movement of a hand is associated with the cortical hand representation. But fine movement of the hand arises from the basal ganglia deep in the brain. How slow or fast to move the hand, when and how to stop are types of information that are generated deep in the brain. Hence, BCI capable of handling specialized sensory signals and signals due to fine motor movements will have to recognize and localize EEG signals arising both from deep and surface locations in the brain. Depth information is best obtained from invasive BCI. Surface information can be obtained from non-invasive BCI. This disclosure describes a technique that uses depth and cortical surface EEG information to drive a non-invasive BCI. The technique in the present disclosure uses the six properties outlined above.

FIG. 1 illustrates an example of using scalp EEG information to drive a non-invasive BCI. Specifically, this figure shows a subject wearing an EEG recording device 110, an EEG signal processor 120, and a device 130. In one embodiment, the EEG signal processor 120 is part of the EEG recording device 110. In one embodiment, the EEG signal processor 120 is part of the device 130. In one embodiment, both the EEG recording device 110 and the EEG signal processor 120 are part of the device 130.

The EEG recording device 110 includes multiple electrodes or contacts (e.g., contact 150) that are placed on the scalp of the subject. In one embodiment, the EEG recording device 110 has an array of 256 contacts but may include more or fewer contacts, for example, from 100-400, or from 200-300, or from 240-260. The EEG recording device 110 records electrical activity along the scalp of the subject. Each contact of the EEG recording device 110 produces an electrical signal. The collection of the analog electrical signals produced by all the contacts of the EEG recording device 110 (except the ground contact) is 2D EEG data 115.

The EEG signal processor 120 receives the analog 2D EEG data 115 and converts it into 3D EEG data 125, i.e., 3D EEG spatial map. Details of this conversion will be further discussed in relation to FIGS. 2-4 below. The device 130 receives the 3D EEG data 125 and performs operations according to the received 3D EEG data. The device 130 can be a computing device or any device that can process the 3D EEG data 125 and function accordingly.

Figure 2:
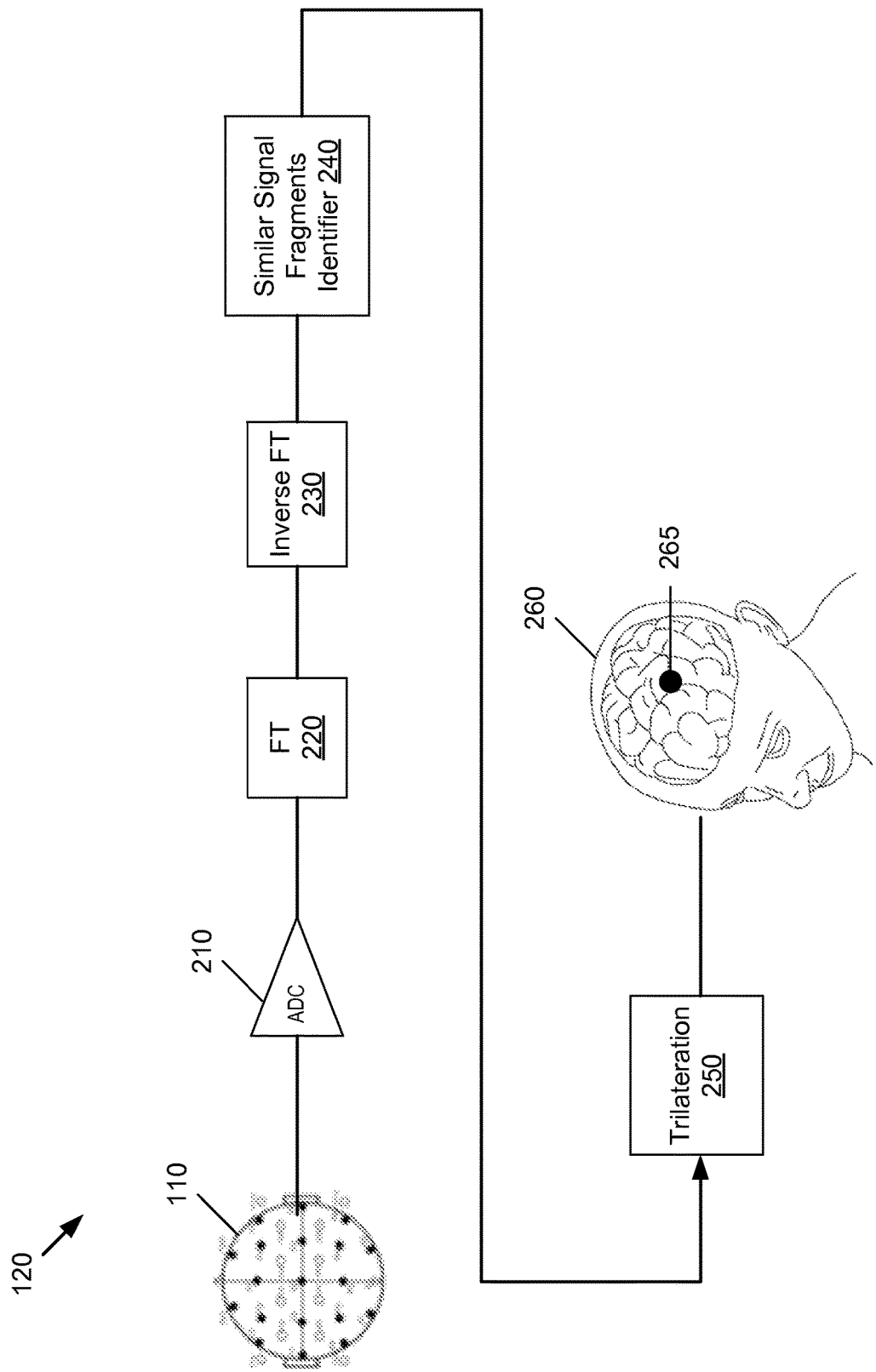
FIG. 2 conceptually illustrates a block diagram of one embodiment of an EEG signal processor that converts 2D EEG data into 3D EEG data.

FIG. 2 conceptually illustrates a block diagram of one embodiment of an EEG signal processor 120 that converts 2D EEG data into 3D EEG data. As shown in FIG. 2, the EEG signal processor 120 includes an analog-to-digital converter (ADC) 210, a Fourier transform (FT) module 220, an inverse FT module 230, a similar signal fragments identifier 240, and a trilateration module 250.

The EEG recording device 110 produces an analog signal for each contact. The collection of signals for all contacts forms the EEG scalp signals, i.e., 2D EEG data. In one embodiment, standard filtering for electromyography (EMG) artifacts is applied to the EEG scalp signals to remove EMG artifacts. In one embodiment, electrooculography (EOG) signals are preserved and will be used in the BCI.

The ADC 210 converts the analog EEG scalp signals into digital signals. For each contact, the FT module 220 then converts the digital signal for that contact from the time domain to the frequency domain. In one embodiment, the FT module 220 uses short-time Fourier transform. For each contact, the inverse FT module 230 selects several frequency bands of interest to the BCI in the frequency domain and converts EEG signals in each of the selected frequency bands back to the time domain to generate several waveforms in the time domain. In one embodiment, each of the waveforms corresponds to a particular frequency band EEG signal that is received at a particular contact. In another embodiment, some contacts may pick up signals from multiple neurons that are separated by distance. These neurons may be signaling at the same frequency, but with different phases. In some embodiments, groupings of contacts located in the same general area (e.g., groups of proximate contacts) may be examined to determine the direction of signaling neurons that overlap in frequency. In particular, time delays between similar frequency components of signals detected by proximate contacts may indicate the direction of a first signaling neuron. Similarly, time delays between similar frequency components of signals detected by proximate contacts may indicate the direction of a second signaling neuron. Based on these directional characteristics, when determining the location/position of the first neuron, the system may ignore signals from the direction of the second neuron. Thereafter, the location/position of the second neuron may be determined by similarly ignoring signals from the direction of the first neuron. In one embodiment, the inverse FT module uses inverse short-time Fourier transform.

The similar signal fragments identifier 240 identifies similar signal fragments across contacts for signals that are in the same frequency band. In one embodiment, the similar signal fragments identifier 240 takes the first derivative for each of the waveforms generated by the inverse FT module 230. This allows these frequency band signals to be compared regardless of signal amplitude differences. The similar signal fragments identifier 240 then compares the first derivatives to identify similar signal fragments. The similar signal fragments identifier 240 is thus able to identify the relative time delay in frequency band signal arrival at the contacts based on the identified similar signal fragments and a faithful representative map of the contacts on the scalp. One possible embodiment of the process of obtaining this faithful map of contacts on the scalp is using plain X-Rays of the skull with the contacts. Another embodiment of this faithful map of contacts on the scalp uses Computer Generated Imagery (CGI), including a CT scan.

For each of the frequency bands that have similar signal fragments, the trilateration module 250 selects a set of contacts that have similar signal fragments in the frequency band. Based on the locations of the selected set of contacts, as well as the relative time delay in frequency band signal arrival at the selected set of contacts, the trilateration module 250 computes a unique location in the depth or surface of the brain using the method of trilateration. In one embodiment, the set of contacts has five contacts. In another embodiment, the set of contacts has four contacts. In yet another embodiment, the set of contacts has more than five contacts. In one embodiment, the number of contacts for trilateration is determined on the fly.

The interference of multiple neuron signals at the same frequency but emitted from disparate locations in the brain can be differentiated from one another by the use of additional electrodes, corresponding to the number of degrees of freedom created by these signals of "multiplicity". That is, two neurons emitting the same frequency signal at disparate locations in the brain will create a single additional degree of freedom, requiring the data of a single extra electrode to solve the system of equations describing the intersection of spheres for trilateration, while three neurons firing simultaneously would require six additional electrodes' data. Image 260 shows an example of the unique location 265 in the depth of the brain identified by the trilateration module 250.

The EEG signal processor 120 was described above for one embodiment of the invention. One of ordinary skill in the art will realize that in other embodiments, this module can be implemented differently. For instance, in one embodiment described above, certain modules are implemented as software modules. However, in another embodiment, some or all of the modules of the EEG signal processor 120 might be implemented by hardware, which can be dedicated application specific hardware (e.g., an ASIC chip or component) or a general purpose chip (e.g., a microprocessor or FPGA).

Figure 3:
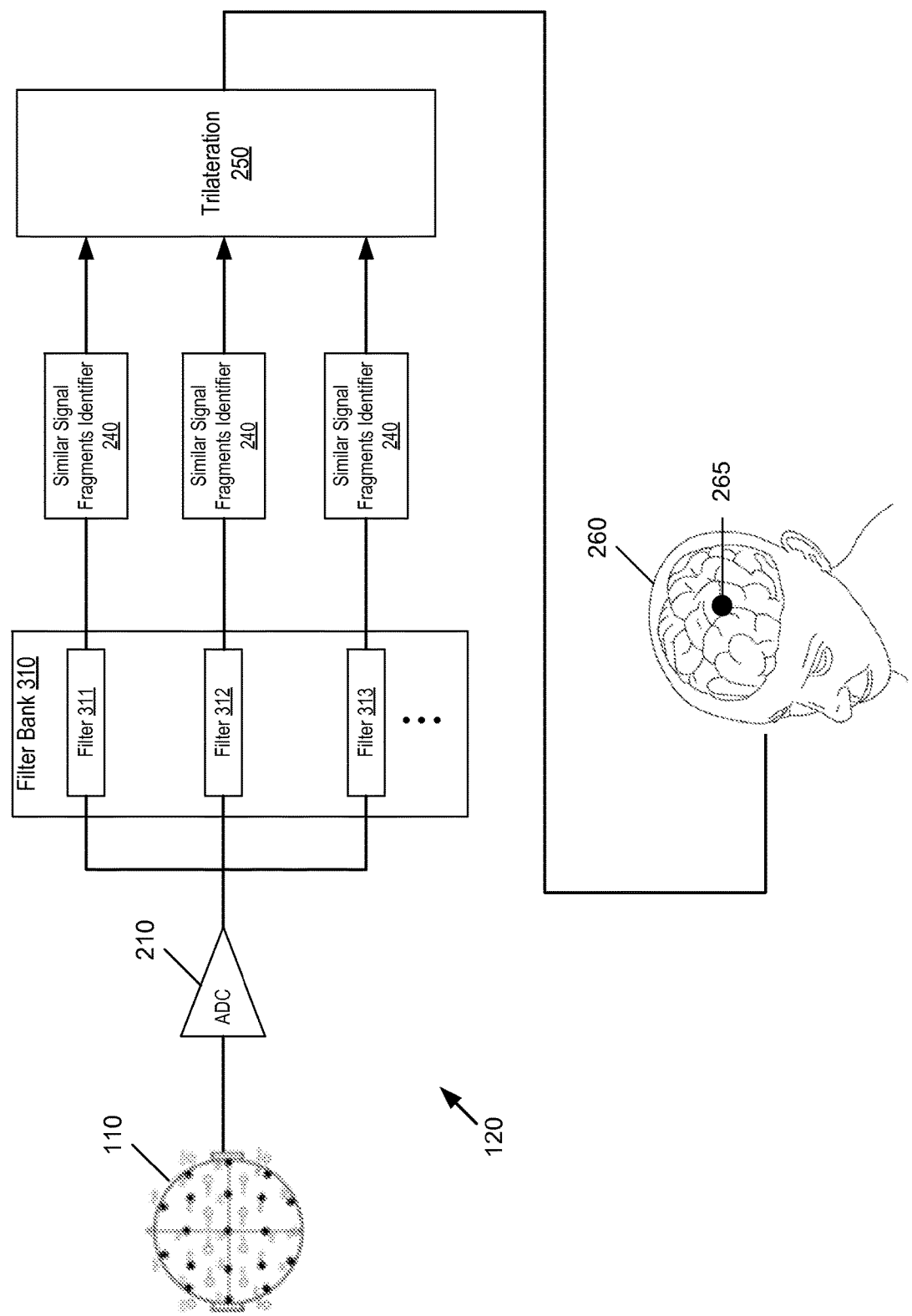
FIG. 3 conceptually illustrates a block diagram of another embodiment of an EEG signal processor that converts 2D EEG data into 3D EEG data.

FIG. 3 conceptually illustrates a block diagram of another embodiment of an EEG signal processor 120 that converts 2D EEG data into 3D EEG data. As shown in FIG. 3, the EEG signal processor 120 includes an analog-to-digital converter (ADC) 210, a filter bank 310, several similar signal fragments identifiers 240, and a trilateration module 250.

The EEG recording device 110 produces an analog signal for each contact. The collection of signals for all contacts forms the EEG scalp signals, i.e., 2D EEG data. In one embodiment, standard filtering for EMG artifacts is applied to the EEG scalp signals to remove EMG artifacts. In one embodiment, EOG signals are preserved and will be used in the BCI.

The ADC 210 converts the analog EEG scalp signals into digital signals. The filter bank 310 is an array of band-pass filters 311-313 that separate each digital EEG signal into multiple channels, each one carrying a single frequency sub-band of the original EEG signal. In one embodiment, each channel created by the filter bank 310 carries a signal at a frequency band of interest to the BCI. In one embodiment, each frequency band signal generated by the filter bank 310 corresponds to a particular frequency band EEG signal that is received at a particular contact. In another embodiment, some contacts may pick up signals from multiple neurons that are separated by distance. These neurons may be signaling at the same frequency, but with different phases.

The similar signal fragments identifier 240 identifies similar signal fragments across contacts for signals that are in the same frequency band. In one embodiment, the similar signal fragments identifier 240 takes the first derivative for each of the frequency band signals. This allows these frequency band signals to be compared regardless of signal amplitude differences. The similar signal fragments identifier 240 then compares the first derivatives to identify similar signal fragments. The similar signal fragments identifier 240 is thus able to identify the relative time delay in frequency band signal arrival at the contacts based on the identified similar signal fragments. For example, the similar signal fragments identifier 240 can identify similar signal fragments across contacts in the frequency band signals outputted by the band-pass filter 311 that carries signals at a particular frequency band.

For each of the frequency bands that have similar signal fragments, the trilateration module 250 selects a set of contacts that have similar signal fragments in the frequency band. Based on the locations of the selected set of contacts, as well as the relative time delay in frequency band signal arrival at the selected set of contacts, the trilateration module 250 computes a unique location in the depth or surface of the brain using the method of trilateration. In one embodiment, the set of contacts has five contacts. In another embodiment, the set of contacts has four contacts. In yet another embodiment, the set of contacts has more than five contacts. In one embodiment, the number of contacts for trilateration is determined on the fly.

The interference of multiple neuron signals at the same frequency but emitted from disparate locations in the brain can be differentiated from one another by the use of additional electrodes, corresponding to the number of degrees of freedom created by these signals of "multiplicity". That is, two neurons emitting the same frequency signal at disparate locations in the brain will create a single additional degree of freedom, requiring the data of a single extra electrode to solve the system of equations describing the intersection of spheres for trilateration, while three neurons firing simultaneously would require six additional electrodes' data. Image 260 shows an example of the unique location 265 in the depth of the brain identified by the trilateration module 250.

The EEG signal processor 120 was described above for one embodiment of the invention. One of ordinary skill in the art will realize that in other embodiments, this module can be implemented differently. For instance, in one embodiment described above, certain modules are implemented as software modules. However, in another embodiment, some or all of the modules of the EEG signal processor 120 might be implemented by hardware, which can be dedicated application specific hardware (e.g., an ASIC chip or component) or a general purpose chip (e.g., a microprocessor or FPGA).

Figure 4:
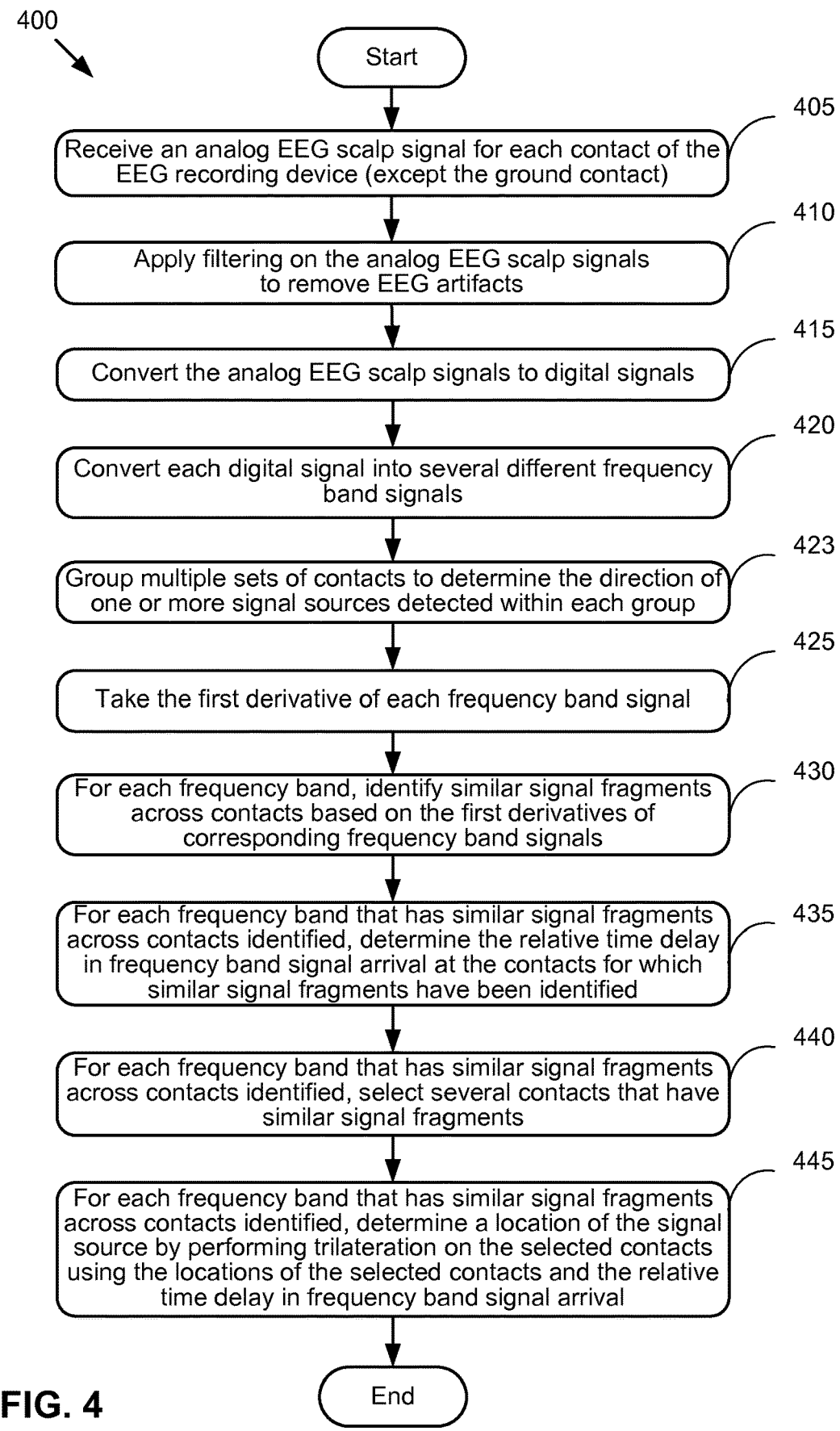
FIG. 4 is a flowchart of one embodiment of converting 2D EEG data into 3D EEG data.

FIG. 4 is a flowchart of one embodiment of converting 2D EEG data into 3D EEG data. In one embodiment, the process 400 is performed by the EEG signal processor 120 described in relation to FIGS. 1-3 above. As shown in the figure, the process 400 begins by receiving, at block 405, an analog EEG scalp signal for each contact of the EEG recording device (except the ground contact). In one embodiment, the EEG recording device is the EEG recording device 110 described in relation to FIGS. 1-3 above.

At block 410, the process 400 applies filtering on the analog EEG scalp signals to remove EMG artifacts. The process 400, at block 415, converts the analog EEG scalp signals to digital signals. In one embodiment, the operations of block 415 are performed by the ADC 210 described in relation to FIGS. 2 and 3 above.

The process 400, at block 420, converts each digital signal into several different frequency band signals. In one embodiment, each frequency band signal corresponds to a particular frequency band EEG signal that is received at a particular contact. In one embodiment, some contacts may pick up signals from multiple neurons that are separated by distance. These neurons may be signaling at the same frequency, but with different phases. In one embodiment, the operations of block 420 are performed by the FT module 220 and inverse FT module 230 described in relation to FIG. 2 above. In another embodiment, the operations of block 420 are performed by the filter bank 310 described in relation to FIG. 3 above.

In some embodiments, groups of proximate contacts may be selected to determine the direction of signals/neurons at block 423. For example, four groups of four contacts may be selected. In other embodiments, different numbers of groups and numbers of contacts may be used. Within each group of contacts, the time difference between frequency bands for each signal associated with these contacts may be compared to determine the direction of a neuron or another source. As will be described in greater detail below, the directional information may be passed into trilateration along with signals from each group with the highest degree of similarity such that signals from particular neurons may be isolated. At block 425, the process 400 takes the first derivative of each frequency band signal. For each frequency band, the process 400 identifies, at block 430, similar signal fragments across contacts based on the first derivatives of corresponding frequency band signals. In some embodiments, this may be restricted to contacts from groups with the highest signal-to-noise ratio (SNR). Next, for each frequency band that has similar signal fragments across contacts identified, the process 400 determines, at block 435, the relative time delay in frequency band signal arrival at the contacts for which similar signal fragments have been identified. In one embodiment, the operations in blocks 425-435 are performed by the similar signal fragments identifier 240 described in relation to FIGS. 2 and 3 above.

For each frequency band that has similar signal fragments across contacts identified, the process 400 selects, at block 440, several contacts that have similar signal fragments. In one embodiment, five contacts having similar signal fragments at a frequency band are selected. In another embodiment, four contacts having similar signal fragments at a frequency band are selected. In yet another embodiment, more than five contacts having similar signal fragments at a frequency band are selected. In one embodiment, the number of contacts selected is determined on the fly.

For each frequency band that has similar signal fragments across contacts identified, the process 400 determines, at block 445, a location of the signal source in the depth or surface of the brain by performing trilateration on the selected contacts using the locations of the selected contacts and the relative time delay in frequency band signal arrival. The relative time delay can be used to derive the relative radius of the sphere for each contact. In one embodiment, the operations of blocks 440 and 445 are performed by the trilateration module 250 described in relation to FIGS. 2 and 3 above. As noted above, directional information may be passed into the trilateration module 250 such that signals originating from particular sources may be isolated during analysis. The process 400 then ends.

One of ordinary skill in the art will recognize that the process 400 is a conceptual representation of the operations used to convert 2D EEG data into 3D EEG data. The specific operations of the process 400 may not be performed in the exact order shown and described. The specific operations may not be performed in one continuous series of operations, and different specific operations may be performed in different embodiments. Furthermore, the process could be implemented using several sub-processes, or as part of a larger macro process.

Figure 5:
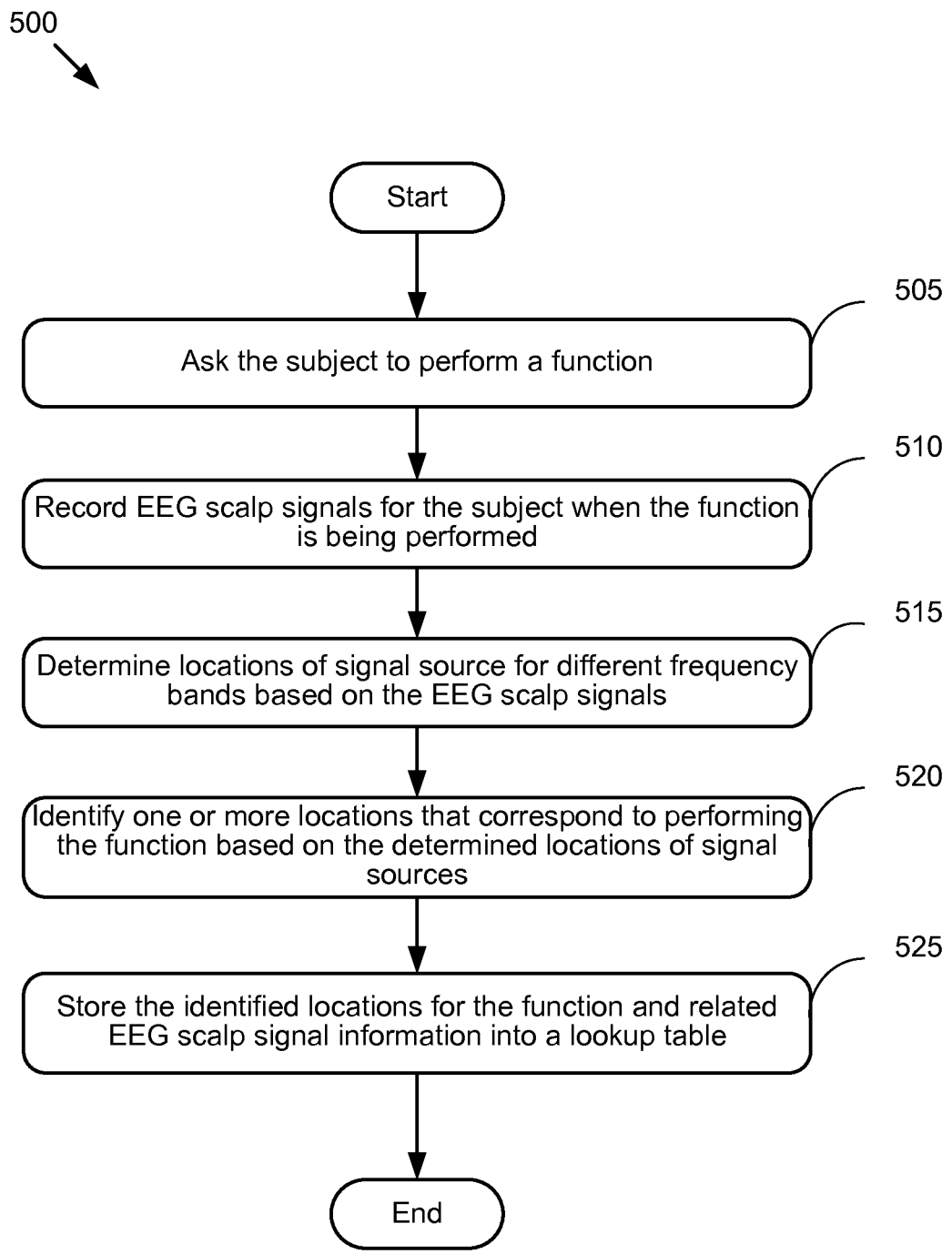
FIG. 5 is a flowchart of one embodiment of generating a mapping between human function and 3D EEG signal information in order to drive a non-invasive BCI.

FIG. 5 is a flowchart of one embodiment of generating a mapping between human function and 3D EEG signal information in order to drive a non-invasive BCI. In one embodiment, process 500 is performed by the device 130 described in relation to FIG. 1 above. As shown in the figure, the process 500 begins by asking, at block 505, the subject to perform a function. The function can be any human function, such as opening the eyes, closing eyes, gazing at a picture, tapping hand, flexion of wrist, flexion/extension of elbow, abduction/adduction of shoulder, plantar-flexion/dorsiflexion of ankle, flexion/extension of knee, abduction/adduction of hip, and flexion/extension of hip. The function can also be an imagined movement. Moreover, the function can be sensing a color, imagining a color, hearing a sound, imagining a sound, etc.

At block 510, the process 500 records EEG scalp signals for the subject when the function is being performed. At block 515, the process 500 determines locations of signal sources in the depth or surface of the brain for different frequency bands based on the EEG scalp signals. In one embodiment, the operations of block 515 are the operations of process 400 described in relation to FIG. 4 above.

The process 500, at block 520, identifies one or more locations that correspond to performing the function based on the determined locations of signal sources. At block 525, the process 500 stores the identified locations for the function and related EEG scalp signal information, i.e., the 3D EEG information, in a lookup table. In one embodiment, the 3D EEG information for a function may include locations of signal sources in the depth or surface of the brain that perform the function, the frequency and amplitude of the signals related to the function, etc. The process 500 then ends. The process 500 can be repeated for different functions to generate an extensive mapping between human function and 3D EEG information.

One of ordinary skill in the art will recognize that the process 500 is a conceptual representation of the operations used to generate a mapping between human function and 3D EEG information. The specific operations of the process 500 may not be performed in the exact order shown and described. The specific operations may not be performed in one continuous series of operations, and different specific operations may be performed in different embodiments. Furthermore, the process could be implemented using several sub-processes, or as part of a larger macro process.

Figure 6:
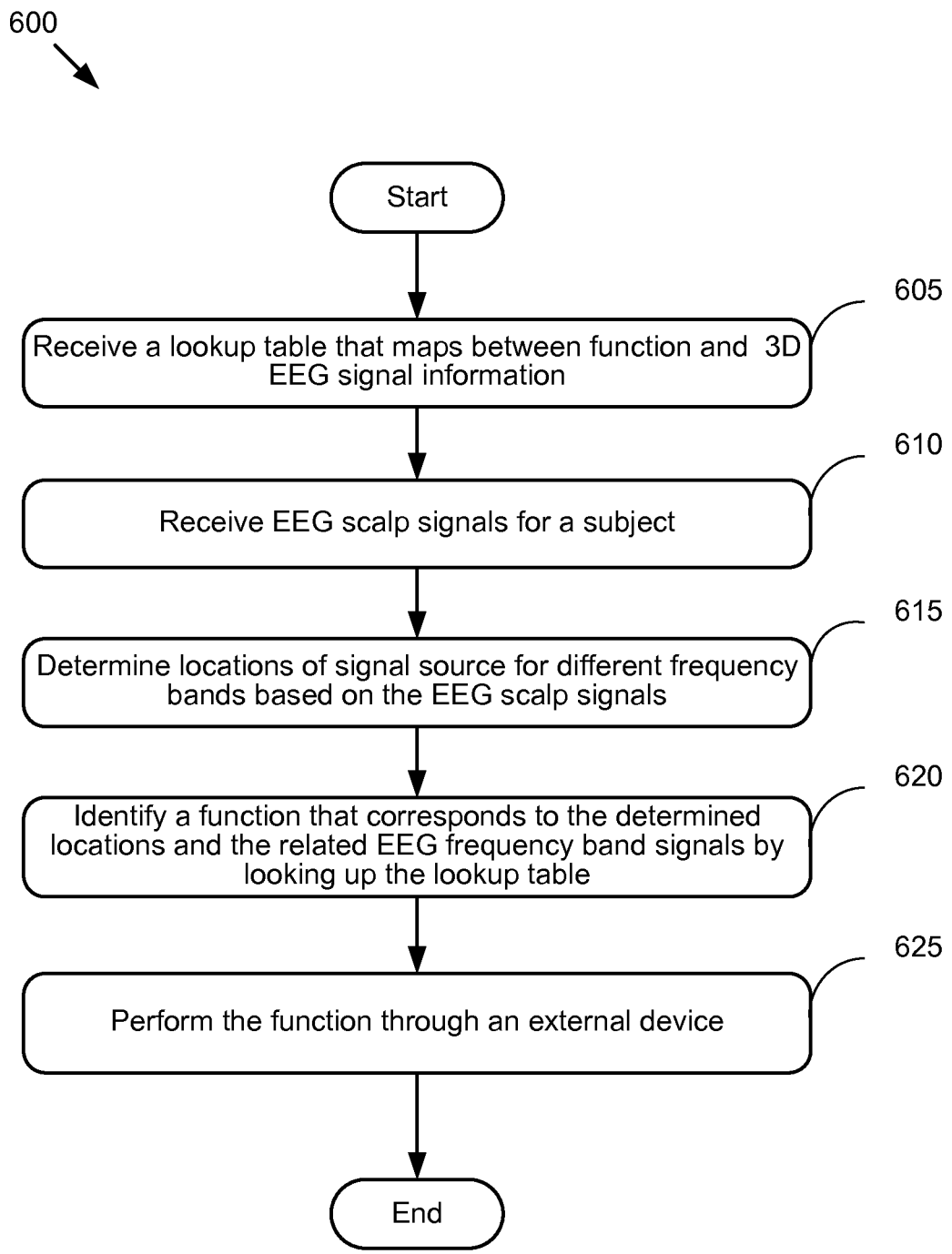
FIG. 6 is a flowchart of one example of applying the mapping between human function and 3D EEG information in driving a non-invasive BCI.

FIG. 6 is a flowchart of one example of applying the mapping between human function and 3D EEG information in driving a non-invasive BCI. Specifically, this figure describes a process 600 that converts EEG scalp signals into 3D EEG signals in order to identify a human function by looking up the mapping between human function and 3D EEG information. In one embodiment, the process 600 is performed by the device 130 described in relation to FIG. 1 above. In one embodiment, the process 600 starts after the mapping has been generated, e.g., by the process described in relation to FIG. 5 above. As shown in the figure, the process 600 begins by receiving, at block 605, a lookup table that maps between each function and its related 3D EEG signal information. In one embodiment, the mapping was generated by the process 500 described in relation to FIG. 5 above.

At block 610, the process 600 receives EEG scalp signals for a subject. At block 615, the process 600 determines locations of signal sources for different frequency bands based on the EEG scalp signals. In one embodiment, the operations of block 615 are the operations of process 400 described in relation to FIG. 4 above.

The process 600, at block 620, identifies a function that corresponds to the determined locations and the related EEG frequency band signals by searching the lookup table. At block 625, the process 600 performs the function through an external device. In one embodiment, the external device is the device 130 described in relation to FIG. 1 above. In one embodiment, the external device may evoke motor movements, visual perception, or speech. The process 600 then ends.

One of ordinary skill in the art will recognize that the process 600 is a conceptual representation of the operations used to apply the mapping between human function and 3D EEG information in driving a non-invasive BCI. The specific operations of the process 600 may not be performed in the exact order shown and described. The specific operations may not be performed in one continuous series of operations, and different specific operations may be performed in different embodiments. Furthermore, the process could be implemented using several sub-processes, or as part of a larger macro process.

Figure 7:
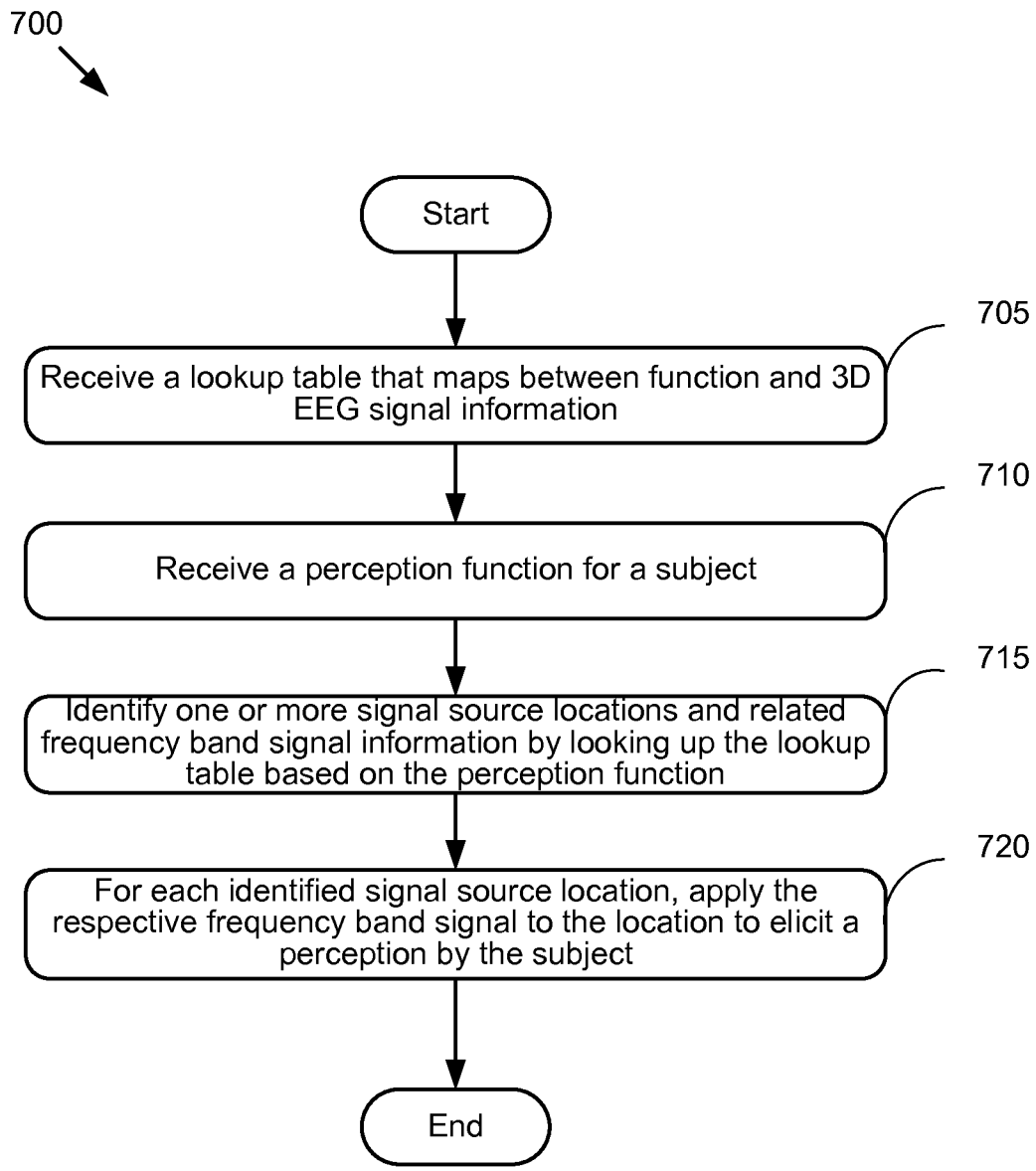
FIG. 7 is a flowchart of another example of applying the mapping between human function and 3D EEG information in driving a non-invasive BCI.

FIG. 7 is a flowchart of another example of applying the mapping between human function and 3D EEG information in driving a non-invasive BCI. Specifically, this figure describes a process 700 that converts a perception function into 3D EEG signals by looking up the mapping between human function and 3D EEG information and uses the 3D EEG information to elicit a perception from a subject. In one embodiment, the process 700 starts after the mapping has been generated, e.g., by the process described in relation to FIG. 5 above. As shown in the figure, the process 700 begins by receiving, at block 705, a lookup table that maps between human function and 3D EEG signal information. In one embodiment, the mapping was generated by the process 500 described in relation to FIG. 5 above.

At block 710, the process 700 receives a perception function for a subject. In one embodiment, the perception function can be hearing a particular sound, seeing a particular color, etc. At block 715, the process 700 identifies one or more signal source locations and related frequency band signal information by searching the lookup table based on the perception function.

For each identified signal source location, the process 700, at block 720, applies the respective frequency band signal to the location to elicit a perception from the subject. The process 700 then ends.

One of ordinary skill in the art will recognize that the process 700 is a conceptual representation of the operations used to apply the mapping between human function and 3D EEG information in driving a non-invasive BCI. The specific operations of the process 700 may not be performed in the exact order shown and described. The specific operations may not be performed in one continuous series of operations, and different specific operations may be performed in different embodiments. Furthermore, the process could be implemented using several sub-processes, or as part of a larger macro process.

The technique described in this disclosure is aimed at building a foundation for depth and cortical EEG analysis using non-invasive methods. This foundation will serve as the starting point for several applications.

One application of embodiments of this technique is stroke. Stroke syndromes can be quite varied and affect different functions based on the stroke territory. Deep brain strokes can be just as devastating in one's life as cortical strokes. Strokes can be due to vascular causes, clotting abnormalities, trauma, infection, neoplasm, drug induced, or congenital causes. A true neuroprosthesis should be able to address the various types of neurological deficits resulting from the different types of strokes and strokes in different locations.

Consider, for example, a stroke affecting the Anterior Choriodal artery territory resulting in contralateral leg plegia. It then becomes important to read inter-hemispheric EEG. This is difficult using standard scalp EEG. However, using scalp EEG data, a computation of depth EEG in the interhemispheric region can provide the necessary information.

Consider a purely subcortical stroke, which usually results in hemiparesis, hemiplegia, and loss of fine motor control. The hemiparesis or hemiplegia resulting from this stroke can be addressed by the various EEG based approaches to brain machine interfaces. This is because the cortical grey matter is still active and EEG signals from the cortex can still be picked up on the scalp. On the other hand, consider a cortical stroke. Such a stroke will result, for example, in neglect, aphasia and hemianopia. Neuroprosthesis for such strokes would require knowledge of deep brain EEG. For example, depth signals from the supplementary motor area could provide the necessary information regarding intent to move, and depth signals from Basal Ganglia would provide information on fine motor control of intended gross movement.

Another application of embodiments of this technique is evoked motor responses. EEG has often been thought as a purely passive recording of brain electrical activity. With 3D EEG information, transcranial electrical or magnetic stimulation aimed at the right location in the brain can be used to elicit motor responses. Neuroprosthesis can have the potential for inducing motor movements, visual perception and speech.

Yet another application of embodiments of this technique is sound perception. For example, people who are congenitally deaf due to dysfunction of proximal auditory apparatus may still have their auditory cortex intact. It is currently possible to map surface evoked EEG responses to auditory stimuli. However, speech involves integration of cortical and subcortical signals. Using the technique developed in this disclosure, it will be possible to identify deep as well as surface EEG signals associated with specific auditory stimuli. This will then enable a reverse transcranial stimulation of the auditory centers in the brain to provide a rich perception of sound for the congenitally deaf.

Another application of embodiments of this technique is vision perception. This application can be extended to color perception for people who have blindness due to dysfunction of optic nerve pathways proximal to the visual cortex. In general, colors and sounds reside in subcortical brain. Once colors and sounds are mapped, transcranial signals can be sent to those locations to elicit color and sound perceptions.

Another application of embodiments of this technique is epilepsy. Currently, depth electrodes are implanted to identify the location and characteristics of epileptic seizures. The practice of identifying seizures is unlikely to change in the near or far future, as this is an essential part of non-medical targeted management of epilepsy. The implantation of multiple depth electrodes (often 15-20 electrodes at a time) carries with it significant risks of iatrogenic strokes, hemiparesis, meningitis, brain abscesses, exacerbation of seizures and death. A non-invasive technique of deriving depth signals from scalp signals is an invaluable advancement in the management of epilepsy. Currently, about 0.5% of population is candidate for epilepsy surgery. The accuracy and efficacy of obtaining depth signal data is an integral part of surgical management of epilepsy. In addition to the risks of the procedure for obtaining depth signal data, the direct cost of the procedure is very high.

Yet another application of embodiments of this technique is implanted nanocircuits. The design of microcircuits for intracranial implantation will require knowledge and accessibility of depth signals prior to implantation.

Other applications for this technique are further contemplated, including, but not limited to, interactive video/audio gaming applications and other entertainment related applications, operation of complex machinery, including, but not limited to, industrial machinery and machinery used in warfare, as well as robotics.

Many of the methods of the disclosed embodiments may be performed with a digital processing system, such as a conventional, general-purpose computer system. Special purpose computers, which are designed or programmed to perform only one function, may also be used.

Figure 8:
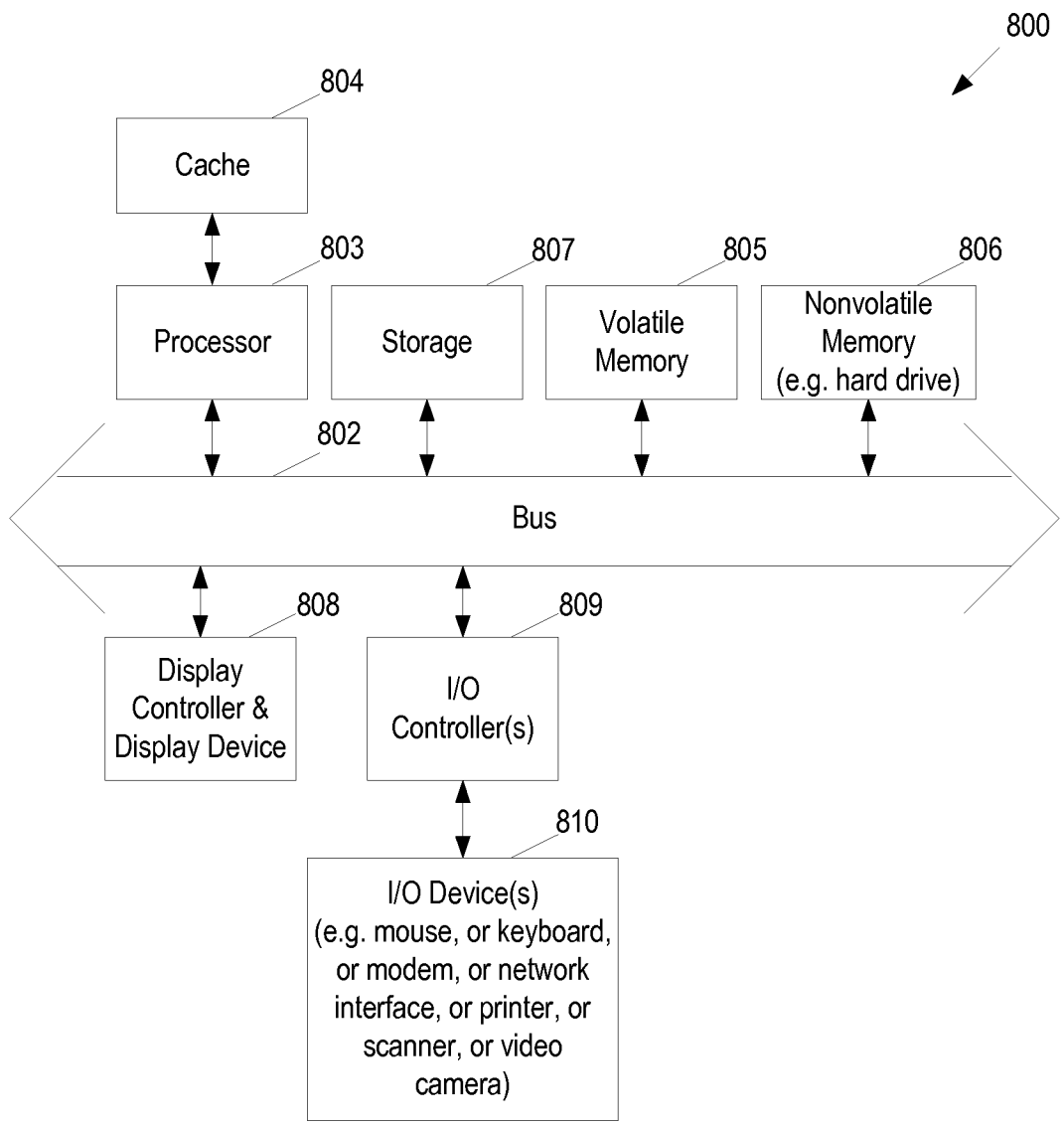
FIG. 8 shows one example of a typical computer system or data processing system that may be used with the disclosed embodiments.

FIG. 8 shows one example of a typical computer system or data processing system that may be used with the disclosed embodiments. For example, in one embodiment the processes described with respect to FIGS. 4-7 are operational through the example of a computing system. However, it is noted that while FIG. 8 illustrates various components of a computer system, it is not intended to represent any particular architecture or manner of interconnecting the components but rather provides an example representation of how the components and architecture may be configured. It will also be appreciated that network computers and other data processing systems that have fewer components or perhaps more components may also be used with the disclosed embodiments. The computer system of FIG. 8 may be any computing system capable of performing the described operations.

As shown in FIG. 8, the computer system 800, which is a form of a data processing system, includes a bus 802, which is coupled to one or more microprocessors 803. In one embodiment, computer system 800 includes one or more of a storage device (e.g., ROM) 807, volatile memory (e.g., RAM) 805, and a non-volatile memory (EEPROM, Flash) 806. The microprocessor 803 is coupled to cache memory 804 as shown in the example of FIG. 8. Cache memory 804 may be volatile or non-volatile memory.

The bus 802 interconnects these various components together and in one embodiment interconnects these components 803, 807, 805, and 806 to a display controller and display device 808. The computer system 800 may further include peripheral devices such as input/output (I/O) devices, which may be mice, keyboards, modems, network interfaces, printers, scanners, video cameras and other devices which are well known in the art. Typically, the input/output devices 810 are coupled to the system through input/output controllers 809.

The volatile memory 805 is typically implemented as dynamic RAM (DRAM) which requires power continually in order to refresh or maintain data in the memory. The non-volatile memory 806 is typically a magnetic hard drive, magnetic optical drive, an optical drive, a DVD RAM, a Flash memory, or other type of memory system which maintains data even after power is removed from the system. Typically, the non-volatile memory will also be a random access memory, although this is not required.

While FIG. 8 shows that the non-volatile memory is a local device coupled directly to the rest of the components in the data processing system, it will be appreciated that the disclosed embodiments may utilize a non-volatile memory which is remote from the system, such as a network storage device which is coupled to the data processing system through a network interface such as a modem or Ethernet interface.

The bus 802 may include one or more buses connected to each other through various bridges, controllers and/or adapters as is well known in the art. In one embodiment the I/O controller 809 includes a USB (Universal Serial Bus) adapter for controlling USB peripherals, and/or an IEEE-1394 bus adapter for controlling IEEE-1394 peripherals.

It will be apparent from this description that aspects of the disclosed embodiments may be embodied, at least in part, in software (or computer-readable instructions). That is, the techniques, for example the processes of FIGS. 4-7, may be carried out in a computer system or other data processing system in response to its processor, such as a microprocessor, executing sequences of instructions contained in a memory, such as storage device 807, volatile memory 805, non-volatile memory 806, cache 804 or a remote storage device. In various embodiments, hardwired circuitry may be used in combination with software instructions to implement the disclosed embodiments. Thus, the techniques are not limited to any specific combination of hardware circuitry and software or to any particular source for the instructions executed by the data processing system. In addition, throughout this description, various functions and operations are described as being performed by or caused by software code to simplify description. However, those skilled in the art will recognize what is meant by such expressions is that the functions result from execution of the code by a processor, such as microprocessor 803.

A machine readable storage medium can be used to store software and data which, when executed by a data processing system, causes the system to perform various methods of the disclosed embodiments. This executable software and data may be stored in various places including, for example, storage device 807, volatile memory 805, non-volatile memory 806 and/or cache 804 as shown in FIG. 8. Portions of this software and/or data may be stored in any one of these storage devices.

Thus, a machine readable storage medium includes any mechanism that stores any information in a form accessible by a machine (e.g., a computer, network device, personal digital assistant, manufacturing tool, any device with a set of one or more processors, etc.). For example, a machine readable medium includes recordable/non-recordable media (e.g., read only memory (ROM); random access memory (RAM); magnetic disk storage media; optical storage media; flash memory devices; etc.).

The detailed description of embodiments of the invention makes reference to the accompanying drawings in which like references indicate similar elements, showing by way of illustration specific embodiments of practicing the invention. Description of these embodiments is in sufficient detail to enable those skilled in the art to practice the invention. One skilled in the art understands that other embodiments may be utilized and that logical, mechanical, electrical, functional and other changes may be made without departing from the scope of the present invention. The detailed description is, therefore, not to be taken in a limiting sense, and the scope of the present invention is defined by the appended claims.

References within the specification to "one embodiment" or "an embodiment" are intended to indicate that a particular feature, structure, or characteristic described in connection with the embodiment is included in at least one embodiment of the present invention. The appearance of the phrase "in one embodiment" in various places within the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments, but not other embodiments.

Some portions of the detailed description were presented as procedures, steps, logic blocks, processing, and other symbolic representations of operations on data bits within a computer memory. These descriptions and representations are the means used by those skilled in the data processing arts to most effectively convey the substance of their work to others skilled in the art. A procedure, computer executed step, logic block, process, etc., is conceived to be a self-consistent sequence of steps or instructions leading to a desired result. The steps are those requiring physical manipulations of physical quantities. Usually, though not necessarily, these quantities take the form of electrical or magnetic signals of a computer readable storage medium and are capable of being stored, transferred, combined, compared, and otherwise manipulated in a computer system. It has proven convenient at times, principally for reasons of common usage, to refer to these signals as bits, values, elements, symbols, characters, terms, numbers, or the like.

In the foregoing specification, the disclosed embodiments have been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed is:

1. A method of deriving depth electroencephalography (EEG) data from non-invasive 2D EEG data with a computer system, the method comprising:
   receiving a plurality of EEG scalp signals, each of the plurality of EEG scalp signals produced by a contact of an EEG recording device;
   converting each of the plurality of EEG scalp signals into a plurality of frequency band signals, the frequency band signals being time-domain signals of select frequency bands;
   identifying, in the frequency band signals, a set of contacts that have same signal fragments for a particular frequency band;
   grouping multiple proximate contacts into multiple groups of contacts;
   for each group of proximate contacts, analyzing the time delays between signals of each contact in the group to determine a direction of a signal source, which is a signaling neuron, relative to the group of contacts; and
   determining a signal source location of the signal source by performing trilateration, including a) determining a relative time delay in signal arrival at the set of contacts based on the same signal fragments in the frequency band signals, b) determining relative radius of sphere for the set of contacts based on the relative time delay, and c) determining the signal source location based on locations of the set of contacts and the relative radius of sphere for the set of contacts, wherein other signal sources which are other signaling neurons detected by the proximate contacts having a direction different from the determined direction of the signal source location are ignored.

2. The method of claim 1, wherein the converting of the plurality of EEG scalp signals into the plurality of frequency band signals includes using a filter bank having an array of band-pass filters to separate each of the plurality of EEG scalp signals into multiple channels, each channel carrying a frequency band of interest in the time-domain.

3. The method of claim 1, wherein the converting of the plurality of EEG scalp signals into the plurality of frequency band signals includes converting each of the plurality of EEG scalp signals into a plurality of frequency domain signals through a set of Fourier transforms, and converting select frequency bands of the frequency domain signals to the time-domain signals of select frequency bands using an inverse Fourier transform.

4. The method of claim 1 further comprising converting the plurality of EEG scalp signals from analog signals into digital signals.

5. The method claim 1, wherein the step identifying of the set of contacts that have same signal fragments comprises:
   taking a first derivative of each frequency band signal; and
   identifying the set of contacts that have same first derivatives in the frequency band signals for the particular frequency band.

6. The method of claim 1, wherein the depth EEG data is created based on the signal source location and the plurality of EEG scalp signals.

7. The method of claim 6 further comprising deriving a relationship between a human function and the depth EEG data.

8. The method of claim 7 further comprising utilizing detected EEG scalp signal changes in a human to drive a machine based on the relationship between human function and the depth EEG data.

9. A non-transitory article of manufacture storing instructions for deriving depth electroencephalography (EEG) data from non-invasive 2D EEG data, wherein the instructions, when performed by a processing device, cause the processing device to:
   process a plurality of EEG scalp signals, each of the plurality of EEG scalp signals produced by a contact of an EEG recording device;
   convert each of the plurality of EEG scalp signals into a plurality of frequency band signals, the frequency band signals being time-domain signals of select frequency bands;
   identify, in the frequency band signals, a set of contacts that have same signal fragments for a particular frequency band;
   group multiple proximate contacts into multiple groups of contacts;
   for each group of proximate contacts, analyze the time delays between signals of each contact in the group to determine a direction of a signal source, which is a signaling neuron, relative to the group of contacts; and
   determine a signal source location of the signal source by performing trilateration, including a) determining a relative time delay in signal arrival at the set of contacts based on the same signal fragments in the frequency band signals, b) determining relative radius of sphere for the set of contacts based on the relative time delay, and c) determining the signal source location based on locations of the set of contacts and the relative radius of sphere for the set of contacts, wherein other signal sources which are other signaling neurons detected by the proximate contacts having a direction different from the determined direction of the signal source location are ignored.

10. The non-transitory article of manufacture of claim 9, wherein the converting of the plurality of EEG scalp signals into the plurality of frequency band signals includes using a filter bank having an array of band-pass filters to separate each of the plurality of EEG scalp signals into multiple channels, each channel carrying a frequency band of interest in the time-domain.

11. The non-transitory article of manufacture of claim 9, wherein the converting of the plurality of EEG scalp signals into the plurality of frequency band signals includes converting each of the plurality of EEG scalp signals into a plurality of frequency domain signals through a set of Fourier transforms, and converting select frequency bands of the frequency domain signals to the time-domain signals of select frequency bands using an inverse Fourier transform.

12. The non-transitory article of manufacture of claim 9 storing further instructions that, when performed by the processing device, cause the processing device to convert the plurality of EEG scalp signals from analog signals into digital signals.

13. The non-transitory article of manufacture of claim 9, wherein the instructions for identifying the set of contacts that have same signal fragments cause the processing device to:
    take a first derivative of each frequency band signal; and
    identify the set of contacts that have same first derivatives in the frequency band signals for the particular frequency band.

14. The non-transitory article of manufacture of claim 9, wherein the locations of the set of contacts is obtained through X-Rays of the set of contacts on the patient.

15. The non-transitory article of manufacture of claim 9, wherein the locations of the set of contacts is obtained using a computed tomography (CT) scan.

16. A system for deriving depth electroencephalography (EEG) data from non-invasive 2D EEG data, the system comprising:
    a set of contacts for placement on a scalp of a patient; and
    an EEG signal processor, including a set of hardware logic circuits configured to:
        receive a plurality of EEG scalp signals, each of the plurality of EEG scalp signals being produced by a contact of an EEG recording device;
        convert each of the plurality of EEG scalp signals into a plurality of frequency band signals, the frequency band signals being time-domain signals of select frequency bands;
        identify, in the frequency band signals, a set of contacts that have same signal fragments for a particular frequency band;
        group multiple proximate contacts into multiple groups of contacts;
        for each group of proximate contacts, analyze the time delays between signals of each contact in the group to determine a direction of a signal source, which is a signaling neuron, relative to the group of contacts; and
        determine a signal source location of the signal source by performing trilateration, including a) determining a relative time delay in signal arrival at the set of contacts based on the same signal fragments in the frequency band signals, b) determining relative radius of sphere for the set of contacts based on the relative time delay, and c) determining the signal source location based on locations of the set of contacts and the relative radius of sphere for the set of contacts, wherein other signal sources which are other signaling neurons detected by the proximate contacts having a direction different from the determined direction of the signal source location are ignored.

17. The method of claim 1, wherein the locations of the set of contacts is obtained through X-Rays of the set of contacts on the patient.

18. The method of claim 1, wherein the locations of the set of contacts is obtained using a computed tomography (CT) scan.

* * * * *